United States Patent
DeBates et al.

(10) Patent No.: US 11,248,949 B2
(45) Date of Patent: Feb. 15, 2022

(54) WIRELESS HAND SENSORY APPARATUS FOR WEIGHT MONITORING

(71) Applicant: Motorola Mobility LLC, Chicago, IL (US)

(72) Inventors: Scott P. DeBates, Crystal Lake, IL (US); Douglas Alfred Lautner, Round Lake, IL (US); Jagatkumar V. Shah, Lake In The Hills, IL (US); Mary Khun Hor-Lao, Chicago, IL (US)

(73) Assignee: Motorola Mobility LLC, Chicago, IL (US)

( * ) Notice: Subject to any disclaimer, the term of this patent is extended or adjusted under 35 U.S.C. 154(b) by 0 days.

(21) Appl. No.: 15/403,155

(22) Filed: Jan. 10, 2017

(65) Prior Publication Data

US 2018/0193699 A1    Jul. 12, 2018

(51) Int. Cl.
   *G01G 19/52* (2006.01)
   *A61B 5/22* (2006.01)
   *A61B 5/00* (2006.01)

(52) U.S. Cl.
   CPC ........... *G01G 19/52* (2013.01); *A61B 5/22* (2013.01); *A61B 5/224* (2013.01); *A61B 5/6806* (2013.01)

(58) Field of Classification Search
   CPC .................................................. G01G 19/52
   USPC ...................................................... 434/247
   See application file for complete search history.

(56) References Cited

U.S. PATENT DOCUMENTS

| | | | | |
|---|---|---|---|---|
| 5,834,706 A | * | 11/1998 | Christ | B07C 5/34 177/1 |
| 2003/0138761 A1 | * | 7/2003 | Pesnell | A63B 59/20 434/247 |
| 2006/0224355 A1 | * | 10/2006 | Morrison | G01G 19/415 702/173 |
| 2008/0204225 A1 | * | 8/2008 | Kitchen | A63B 21/072 340/539.22 |
| 2013/0005534 A1 | * | 1/2013 | Rosenbaum | A43B 3/0015 482/8 |
| 2016/0249832 A1 | * | 9/2016 | Carter | A61B 5/7246 600/595 |
| 2017/0100632 A1 | * | 4/2017 | Castelo Branco | A41D 19/0027 |
| 2018/0182236 A1 | * | 6/2018 | Hor-Lao | A43B 3/0005 |
| 2018/0182253 A1 | * | 6/2018 | Hor-Lao | G09B 5/02 |

* cited by examiner

*Primary Examiner* — Kesha Frisby
(74) *Attorney, Agent, or Firm* — FIG. 1 Patents

(57) ABSTRACT

In aspects of a wireless hand sensory apparatus for weight monitoring, a wearable article is worn by a user who moves items. A tracking system is implemented in the wearable article, and the tracking system includes a force sensor, or force sensors, in the wearable article to register a force on an item. The tracking system includes tracking logic that determines a weight of the item based on the force on the item. The tracking system may also include a motion sensor to sense motion of the wearable article, and the tracking logic determines how the item is moved based on the motion of the wearable article. The tracking logic can also determine the weight of the item based on the force on the item in combination with a speed of the motion of the wearable article.

20 Claims, 5 Drawing Sheets

WIRELESS HAND SENSORY APPARATUS FOR WEIGHT MONITORING

BACKGROUND

The fitness industry continues to expand every year, with many personal fitness devices designed to track overall user fitness, such as heart rate, distance traveled, calories burned, personal fitness goals, sleep tracking, and the like. Most of the personal fitness devices focus on heart rate and pedometers. However, even with the popularity of the many different personal fitness devices, some users, and in particular those who enjoy exercising by lifting weights, still have to track activities and exercises with a pen and notebook, or with data entry in a mobile phone or other portable device. The aspects of lifting weights, to include the amount of weight lifted and the number of reps, are not typically tracked by the various personal fitness devices.

BRIEF DESCRIPTION OF THE DRAWINGS

Aspects of a wireless hand sensory apparatus for weight monitoring are described with reference to the following Figures. The same numbers may be used throughout to reference like features and components that are shown in the Figures.

DETAILED DESCRIPTION

Figure 1:
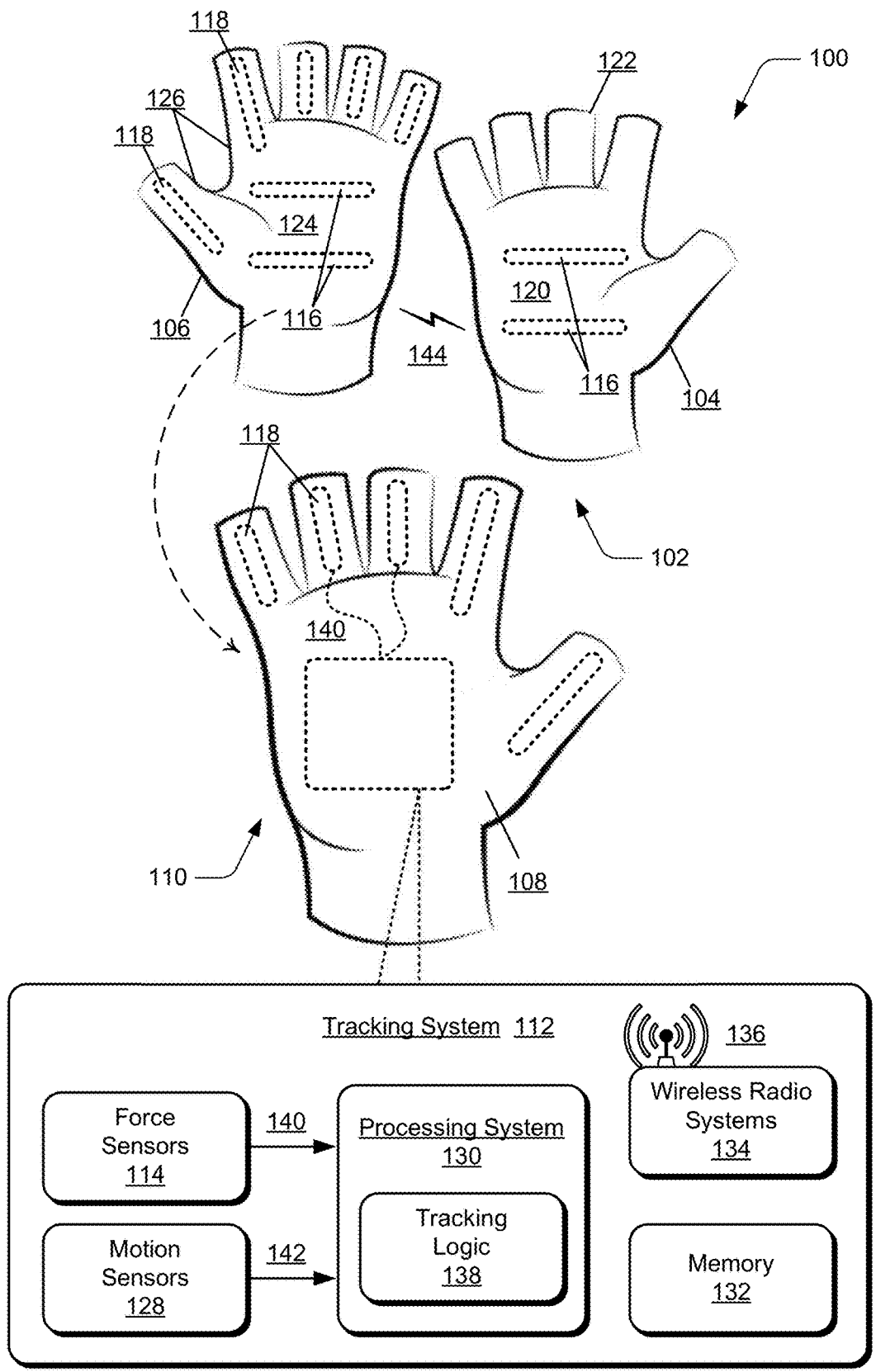
FIG. 1 illustrates an example system in which aspects of a wireless hand sensory apparatus for weight monitoring can be implemented.

A wireless hand sensory apparatus for weight monitoring is described, and may be implemented as a wearable article that is worn by a user who moves items and objects. For example, wearable articles may be a pair of wireless, sensor-based gloves with force sensors integrated in the palm and/or in the fingers of the gloves. The pair of gloves are wearable by a user who pushes or grasps and moves items, and a tracking system is implemented in at least one glove of the pair of gloves. The pair of gloves implemented as the wireless hand sensory apparatus for weight monitoring are designed to be worn by a person who exercises by lifting weights in a gym, or a person who works as a package handler for a package delivery company, either on a delivery route or in a package handling and distribution facility. The pair of gloves implemented as the wireless hand sensory apparatus for weight monitoring may also be applicable for postal workers, or for persons who work as police officers, construction workers, baggage handlers, and in many other professions. Although the wireless hand sensory apparatus is described throughout as being implemented as the pair of gloves, it should be noted that the techniques described herein can be implemented for any form of a wearable article or apparatus on the hand or foot of a user, such as a glove or gloves, and exoskeleton system or apparatus, a bandage or other hand covering, a ring worn by the user, a mechanism (e.g., a sticker) attachable to the palm of a user's hand, a sock or other foot covering, a shoe or boot insert, and/or for any other wearable article, attached item, or mechanism that attaches to an appendage of a user.

The tracking system includes the force sensors in a wearable article to register a force on an item, such as a package, a gym weight, or other objects. The force sensors in the glove can include a palm force sensor, or sensors, as well as finger force sensors. The tracking system also includes tracking logic that determines a weight of the item based on the force on the item. The tracking system may also include a motion sensor to sense motion of the glove, and the tracking logic determines how the item is moved based on the motion of the wearable article. The tracking logic can also determine the weight of the item based on the force on the item in combination with a speed of the motion of the wearable article. Further, the tracking system may be implemented in both gloves of a pair of gloves as the wearable articles, and the tracking system includes a wireless radio system to synchronize tracking data between the tracking systems of the pair of gloves. The tracking logic can then determine a weight distribution of the weight of the item based on the force on the item registered by each of the respective gloves.

In aspects of a wireless hand sensory apparatus for weight monitoring, the tracking logic of the tracking system can determine physical characteristics of the user who wears the wearable article, such as a lifting technique of the user to lift and move an item. The physical characteristics of the user can also include a distance traveled over a time duration, such as the distance walked by a user in a package handling facility. The tracking logic can generate user feedback that indicates a proper lifting technique of an item based on the force on the item and the motion of the wearable article. Further, the tracking logic can determine that the motion is a repetitive motion for a number of repetitions, and correlates the repetitive motion with an exercise.

In other aspects of a wireless hand sensory apparatus for weight monitoring, the item that the user moves may be a package for delivery, and the tracking logic verifies contents of the package based on the weight of the package. The tracking logic can also determine package handling activity for the package based on the force and the motion of the wearable article as the package is handled. Additionally, the tracking system can include a wireless radio system to communicate tracking data to a device that is in communication with the tracking system of the wearable article.

While features and concepts of a wireless hand sensory apparatus for weight monitoring can be implemented in any number of different devices, systems, environments, and/or configurations, aspects of a wireless hand sensory apparatus for weight monitoring are described in the context of the following example devices, systems, and methods.

FIG. 1 illustrates an example system 100 in which aspects of a wireless hand sensory apparatus for weight monitoring can be implemented, such as a pair of wireless, sensor-based gloves 102 as wearable articles. As noted above, although a wearable article implemented as a wireless hand sensory apparatus is described throughout as a pair of gloves, the techniques described herein can be implemented for any form of a wearable article or apparatus on a hand or foot of a user. The example system 100 includes the pair of gloves 102 that are a right-hand glove 104 and a left-hand glove 106, as viewed from the palm side of the gloves. The back 108 of the left-hand glove 106 is also shown at 110 with the glove flipped over. The pair of gloves 102 are designed to be worn by a user who pushes or grasps and moves items, such as person who exercises by lifting weights in a gym, or a person who works as a package handler for a package delivery company, either on a delivery route or in a package handling and distribution facility. Aspects of a wireless hand sensory apparatus for weight monitoring may also be useful in determining a person's physical viability to perform a particular job, and may be applicable for postal workers, or for persons who work as police officers, construction workers, baggage handlers, and in many other professions.

As noted above, a tracking system 112 integrated with the gloves 102 can detect, sense, and/or determine various characteristics of items that the user moves while wearing the gloves, as well as various physical characteristics related to the user moving the items. For example, the item characteristics that can be determined about an item include the weight and/or size of the item, package weight verification, package content confirmation based on a known weight of the item in a package, evidence of product tampering based on a different weight than the known weight of the item, and various other characteristics about the item.

The physical characteristics related to the user moving an item, or items, that can be determined include a proper lifting form and technique when the user picks up and moves an item, repetitive motions, and an indication of the user having an injury relating to lifting and moving items. The physical characteristics can also include determining the distance traveled over a time duration by a user handling items or packages, package handling activities, efficiencies of lifting and movement, as well as safety concerns and various other physical characteristics related to a user moving an item, or items.

The tracking system 112 can be implemented in one or both gloves of the pair of gloves 102 as wearable articles. Although FIG. 1 generally illustrates the tracking system implemented in the left-hand glove 106, the tracking system 112 may be implemented in the right-hand glove 104, or implemented in both of the gloves of the pair of gloves. Unless specifically indicated, the term "glove" as used herein applies to either of the right-hand glove 104, the left-hand glove 106, or both gloves of the pair of gloves 102.

The tracking system 112 includes a force sensor 114, or force sensors, integrated in the gloves 102 to register a force of a push or grasp on an item when a user pushes or picks up and moves the item. The force sensors 114 in a glove can include a palm force sensor 116, or sensors, as well as finger force sensors 118. For example, the right-hand glove 104 is shown having two palm force sensors 116 integrated in the palm region 120 of the glove. Although the right-hand glove 104 is shown having the two palm force sensors 116, a glove may be implemented with one palm force sensor 116 of the tracking system 112, or with more than two palm force sensors. In an implementation, a glove may include only a palm force sensor 116, or sensors, of the tracking system. The fingers 122 of the right-hand glove 104 do not include finger force sensors in this example.

The left-hand glove 106 is also shown having two palm force sensors 116 integrated in the palm region 124 of the glove. Additionally, the fingers 126 of the left-hand glove 106 include the finger force sensors 118. As generally described herein, the thumb of a glove is referred to collectively as one of the fingers 126 of the glove. Further, although all of the fingers 126 of the left-hand glove 106 are shown having an integrated finger force sensor 118, any number of the fingers 126 of the glove may or may not include a finger force sensor.

In implementations, the tracking system 112 can include a motion sensor 128, or motion sensors, to sense motion of the glove as the user picks up and moves an item while wearing the pair of gloves 102. The tracking system 112 may be implemented with one or various motion sensors 128, such as a gyroscope, an accelerometer, and/or other types of motion sensors to sense motion of the glove in which the tracking system 112 is integrated.

Generally, the tracking system 112 can be implemented with computing and/or electronic device components such as a processing system 130 (e.g., one or more processors), a memory 132, and any number and combination of various components as further described with reference to the example device shown in FIG. 5. Additionally, the tracking system 112 includes a power source, such as a battery, to power the various components of the tracking system.

Further, the tracking system 112 can include various, different wireless radio systems 134, such as for Wi-Fi, Bluetooth™, Mobile Broadband, LTE, Near Field Communication (NFC), or any other wireless radio system or format for communication via respective wireless networks (e.g., the wireless network as described with reference to FIG. 2). Generally, the tracking system 112 implements the wireless radio systems 134 that each include a radio device, antenna 136, and chipset that is implemented for cellular, wireless, and/or other network communication with other devices, networks, and services. A wireless radio system 134 can be configured to implement any suitable communication protocol or standard.

The tracking system 112 includes tracking logic 138 that can be implemented as a software application or module, such as computer-executable software instructions that are executable with a processor (e.g., with the processing system 130). Similarly, the tracking system 112 may also include an operating system as a software application. The tracking system 112 and/or the operating system can be stored on computer-readable storage memory (e.g., the memory 132), such as any suitable memory device or electronic data storage implemented with the tracking system.

In aspects of a wireless hand sensory apparatus for weight monitoring, the tracking logic 138 receives force sensor inputs 140 from the force sensor or sensors 114, and can receive motion sensor inputs 142 from the motion sensor or sensors 128. The tracking logic 138 is implemented to determine the weight of an item based on the force of the grasp on the item by the user who picks up and moves the item. Generally for a heavier weighing item, an increased or more force will be registered by the force sensors 114 as the user exerts more pressure of a grasping force to hold and pick up the item. Conversely for a lighter weighing item, less of a force will be registered by the force sensors 114 as the user applies less pressure of a grasping force to pick up the item. As used herein, the terms "heavier" and "lighter" with reference to an item's weight, as well as "more" and "less" with reference to force applied, are merely relative terms used to illustrate how the grasping force of a user who picks up and moves the item may correlate to a weight of the item.

Further, the tracking logic 138 can be implemented to determine the weight of an item based on the force of the grasp on the item in combination with a speed of the motion of the glove. Generally for a heavier weighing item, the speed of the motion of the glove is likely to be slower than for a lighter weighing item that the user can move easily and quicker. As used herein, the terms "slower" and "quicker" with reference to the speed of motion as an item is moved are merely relative terms used to illustrate how the speed of motion may correlate to a weight of the item as a user picks up and moves the item.

Additionally, as noted above, the tracking system 112 may be implemented in both gloves of the pair of gloves 102, and the wireless radio system 134 in each of the respective tracking systems 112 for the right-hand glove 104 and the left-hand glove 106 can be utilized to synchronize tracking data and the timing of data reporting between the tracking systems of the pair of gloves (at 144). The tracking data can include the force sensor inputs 140, the motion sensor inputs 142, and any other tracking data related to the weight and motion determinations of an item that a user picks up and moves while wearing the pair of gloves 102.

The tracking logic 138 can then determine a weight distribution of the weight of the item based on the force of the grasp on the item registered by each of the tracking systems 112 integrated in the respective left-hand and right-hand gloves. Similarly, the tracking logic 138 can determine which side (e.g., as an arm and hand combination) a user favors or uses more often based on the force distribution applied to grasp the item with each of the respective left-hand and right-hand gloves. A user may favor or limit the use of one side (e.g., an arm and hand combination) or the other, indicating that the user may have an injury.

In aspects of a wireless hand sensory apparatus for weight monitoring, the tracking logic 138 of the tracking system 112 can also be implemented to determine physical characteristics of the user who wears the pair of gloves 102. The physical characteristics of the user can include a lifting technique of the user to lift and move an item, or items, and may also include a determination that the motion is a repetitive motion for a number of repetitions, such as by a user who lifts weights in a gym for exercise. The tracking logic 138 can then correlate the repetitive motion with an exercise, such as based on a database that correlates particular motions with respective exercises.

The tracking logic 138 can also generate user feedback as any type of audio or visual feedback that indicates a proper lifting technique of an item (e.g., weights in a gym, or packages for delivery) based on the force of the grasp on the item and the motion of the glove or gloves as the user picks up and moves the item. The tracking logic 138 can determine the exercise performed for the weight that a user lifts, count the user's reps, and provide user feedback related to the user's lifting form, technique, and any type of other user feedback related to the determined exercise. As noted above, the tracking logic 138 may detect an indication of the user having an arm or hand injury if the user favors or limits the use of one side (e.g., an arm and hand combination) or the other. This information can also be provided as user feedback, not only to the user, but to health and wellness professionals that monitor job site activities and user efficiencies.

In other aspects of a wireless hand sensory apparatus for weight monitoring, the tracking logic 138 can be implemented to determine a physical characteristic of a user as the distance traveled over a time duration, such as the distance walked by a user in a package handling facility as the user picks up and moves packages while wearing the pair of gloves 102. The tracking logic 138 can also determine package handling activity for a package (e.g., an item or a package that contains an item) based on the force of the grasp and the motion of the glove or gloves as the package is handled. Further, the item that the user grasps and moves may be a package for delivery, and the tracking logic 138 can verify contents of the package based on the weight of the package, as determined from the package handling activity based on the force of the grasp and/or the motion of the glove as the package is handled. Additionally, as further described with reference to FIG. 2, an item or package may have an associated wireless tag with wireless capabilities to provide an item identifier for confirmation of an item that has been initially verified based on the weight of the item from the force of the grasp as the user moves and handles the item. As further described with reference to FIG. 2, a wireless radio system 134 of the tracking system 112 can communicate tracking data to another, independent device that is in communication with the tracking system 112 of the glove, or as implemented in both the left-hand and the right-hand gloves of the pair of gloves 102.

Figure 2:
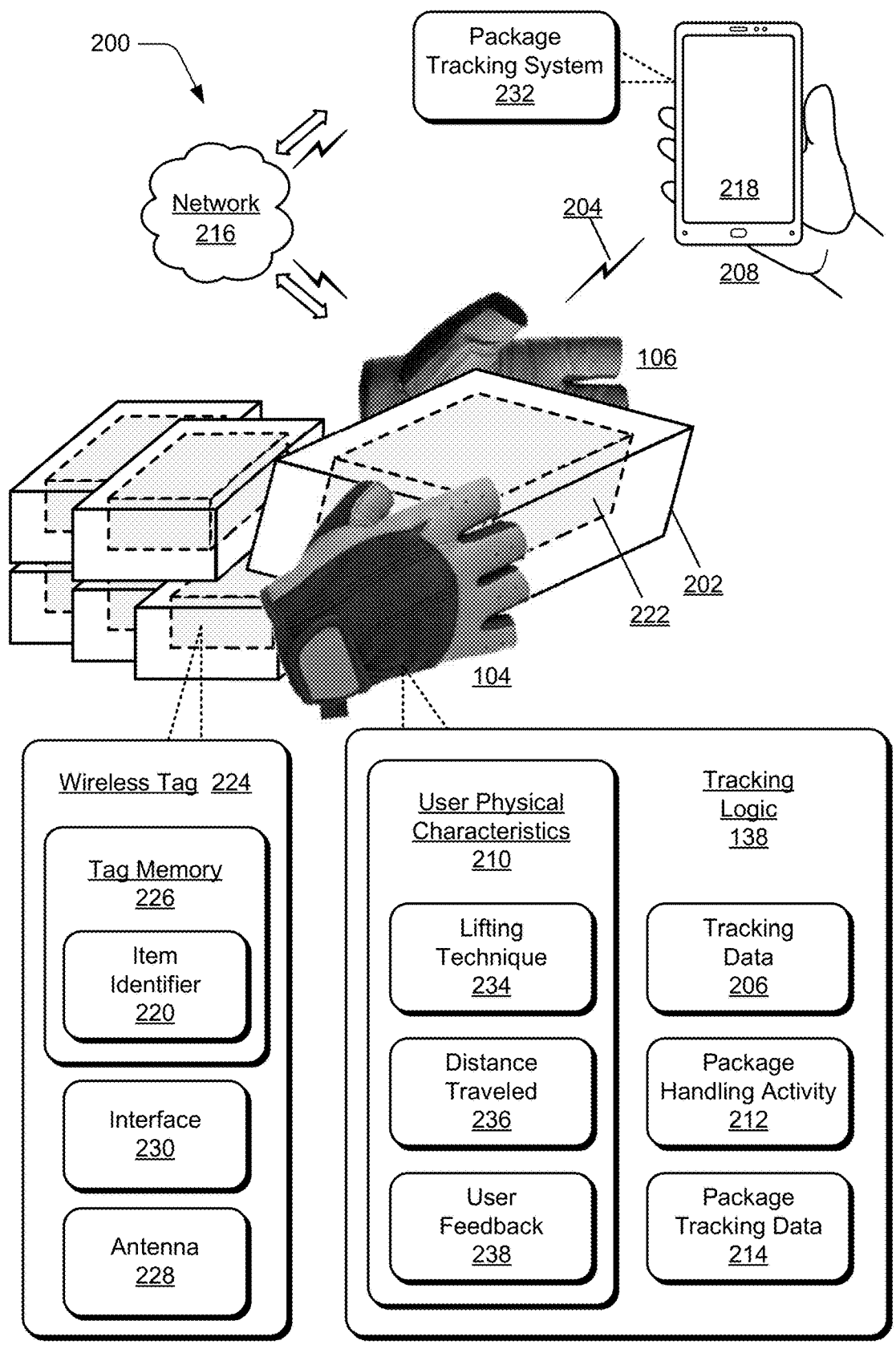
FIG. 2 further illustrates an example system in which aspects of a wireless hand sensory apparatus for weight monitoring can be implemented.

FIG. 2 further illustrates an example system 200 for a wireless hand sensory apparatus for weight monitoring as described with reference to the pair of wireless, sensor-based gloves shown in FIG. 1. As noted above, a user can wear the pair of gloves 102 (i.e., the right-hand glove 104 and the left-hand glove 106 as wearable articles) while lifting weights for exercise, or while handling and moving packages 202 in a package distribution facility or on a delivery route. The tracking system 112 that is integrated in the right-hand glove 104, the left-hand glove 106, or in both gloves of the pair of gloves 102 includes the wireless radio system 134, which can communicate (at 204) the tracking data 206 to another device 208 that is in communication with the tracking system 112 of the glove or gloves. The tracking data 206 can include the user physical characteristics 210, as determined by the tracking logic 138, as well as information related to package handling activity 212. The tracking system 112 can also communicate (at 204) the package tracking data 214 to the device 208 that is in communication with the tracking system 112 of the glove or gloves.

The device 208 may be any type of mobile phone, tablet device, computing device (e.g., portable and desktop computers), consumer electronic device, or other type of computing and electronic device that is implemented to communicate, via a network 216 (e.g., a Wi-Fi network) with the tracking system 112 that is integrated in the glove or gloves 102. The device 208 can be implemented with various components, such as an integrated display device 218, and with any number and combination of various components as further described with reference to the example device shown in FIG. 5.

The network 216 generally represents any type of communication and data network, and any of the server and devices, as well as the tracking system 112 described herein, can communicate via the network 216 (or combination of networks), such as for data communication between the device 208 and the tracking system 112 that is integrated in one or both gloves of the pair of gloves 102. The network 216 can be implemented to include wired and/or wireless network. The network can also be implemented using any type of network topology and/or communication protocol, and can be represented or otherwise implemented as a combination of two or more networks, to include cellular networks, IP-based networks, and/or the Internet. The network 216 may also include mobile operator networks that are managed by a network provider of a cellular network, a mobile network operator, and/or other network operators, such as a communication service provider, mobile phone provider, and/or Internet service provider.

The package tracking data 214 that is communicated to the device 208 can include a unique item identifier 220 of an item 222 or items (e.g., a unique identifier of each of the items), such as in items in the packages 202. The unique item identifier 220 can be received from a wireless tag 224 that is associated with a respective item 222. A wireless tag 224 that is associated with an item can be implemented as any form of a near field communication (NFC) tag, a UHF RFID tag, a BLE tag, and the like. A tag memory 226 in each respective wireless tag 224 can store the unique item identifier 220 for each respective one of the items 222, or the items in the packages 202. Generally, the wireless tags 224 are small electronic tags or labels that can be programmed with data and other information, and may be implemented for one-way or two-way wireless communication, such as to communicate to the tracking system 112 of the pair of gloves 102, or communicate directly to the device 208.

A wireless tag 224 can include an antenna 228, and a transmitter and receiver (or may be implemented as a transceiver) for two-way communication with a tag reader. In response to receipt of an interrogation signal, an ASIC/CPU module of the wireless tag 224 formulates a response that may include data (e.g., the item identifier 220) from the wireless tag, and the response is wirelessly transmitted. The response signals from a wireless tag 224 can be communicated using low frequency (LF), high frequency (HF), or ultra-high frequency (UHF) radio waves. The tag memory 226 (e.g., non-volatile memory) can be accessed via a radio frequency (RF) interface 230 of the wireless tag.

The device 208 can include a package tracking system 232 (e.g., a software application) to track the packages 202 in a package distribution facility or on a delivery route as the user picks up and moves the packages. The package tracking system 232 at the device 208 can receive the package tracking data 214 from the tracking system 112 of the pair of gloves 102 and/or receive the item identifiers 220 from the wireless tags 224 that correspond to the respective items 222. The package tracking data 214 can include the weight and/or size of a package 202, and the package tracking system 232 can then verify the package weight, confirm the package contents based on a known weight of an item 222 or items in the package 202, determine evidence of product tampering based on a different weight than the known weight of the item 222 or items in the package 202, and determine or verify other characteristics about the package.

In implementations, the tracking logic 138 of the pair of gloves 102 can initially validate the weight of an item 222 based on the force sensing when a user wears the pair of gloves 102, such as while lifting weights for exercise, or while handling and moving packages as in this example. The wireless capabilities of an item 222 with a wireless tag 224 can then be used to provide confirmation of an item, such as based on the item identifier 220. The tracking logic 138 of the pair of gloves 102 and/or the package tracking system 232 of the device 208 can verify that an item 222 is an intended item for delivery based on the weight and/or the item identifier 220 of the item.

The device 208 can also receive the user physical characteristics 210 from the tracking system 112 of the pair of gloves 102. The user physical characteristics 210 related to the user moving a package 202, or packages, can include an indication of the lifting technique 234 of the user who picks up and moves an item (e.g., a package, a weight, or any other type of item), the distance traveled 236 over a time duration by a user handling items or packages, and any other package handling activity 212. Information related to the package handling activity 212 can include a determination of repetitive motions, an indication of the user having an injury relating to lifting and moving items, efficiencies of lifting and movement (e.g., related to the lifting technique 234), as well as safety concerns and various other physical characteristics related to a user moving the package 202, or packages.

The user physical characteristics 210 can also include user feedback 238 that is communicated to the device 208 as any type of audio or visual feedback, such as for display on the integrated display device 218 to indicate a proper lifting technique of an item (e.g., weights in a gym, or packages for delivery) based on the force of the grasp on the package 202 and the motion of the glove or gloves as the user picks up and moves the package. In implementations, the user feedback 238 may include any one or more of the tracking data 206, the user physical characteristics 210, information of the package handling activity 212, the package tracking data 214, and any other type of user feedback. Additionally, the user feedback (to include any of the above described information) may be communicated to a cloud-based service via the network 216, where the cloud-based service provides additional services, such as in the form of a virtual trainer that shows proper lifting techniques (e.g., as a video or other images), or provides additional safety input for weight lifting, exercising, package handling, moving items, and the like.

Example methods 300 and 400 are described with reference to respective FIGS. 3 and 4 in accordance with implementations of a wireless hand sensory apparatus for weight monitoring. Generally, any services, components, modules, methods, and/or operations described herein can be implemented using software, firmware, hardware (e.g., fixed logic circuitry), manual processing, or any combination thereof. Some operations of the example methods may be described in the general context of executable instructions stored on computer-readable storage memory that is local and/or remote to a computer processing system, and implementations can include software applications, programs, functions, and the like. Alternatively or in addition, any of the functionality described herein can be performed, at least in part, by one or more hardware logic components, such as, and without limitation, Field-programmable Gate Arrays (FPGAs), Application-specific Integrated Circuits (ASICs), Application-specific Standard Products (ASSPs), System-on-a-chip systems (SoCs), Complex Programmable Logic Devices (CPLDs), and the like.

Figure 3:
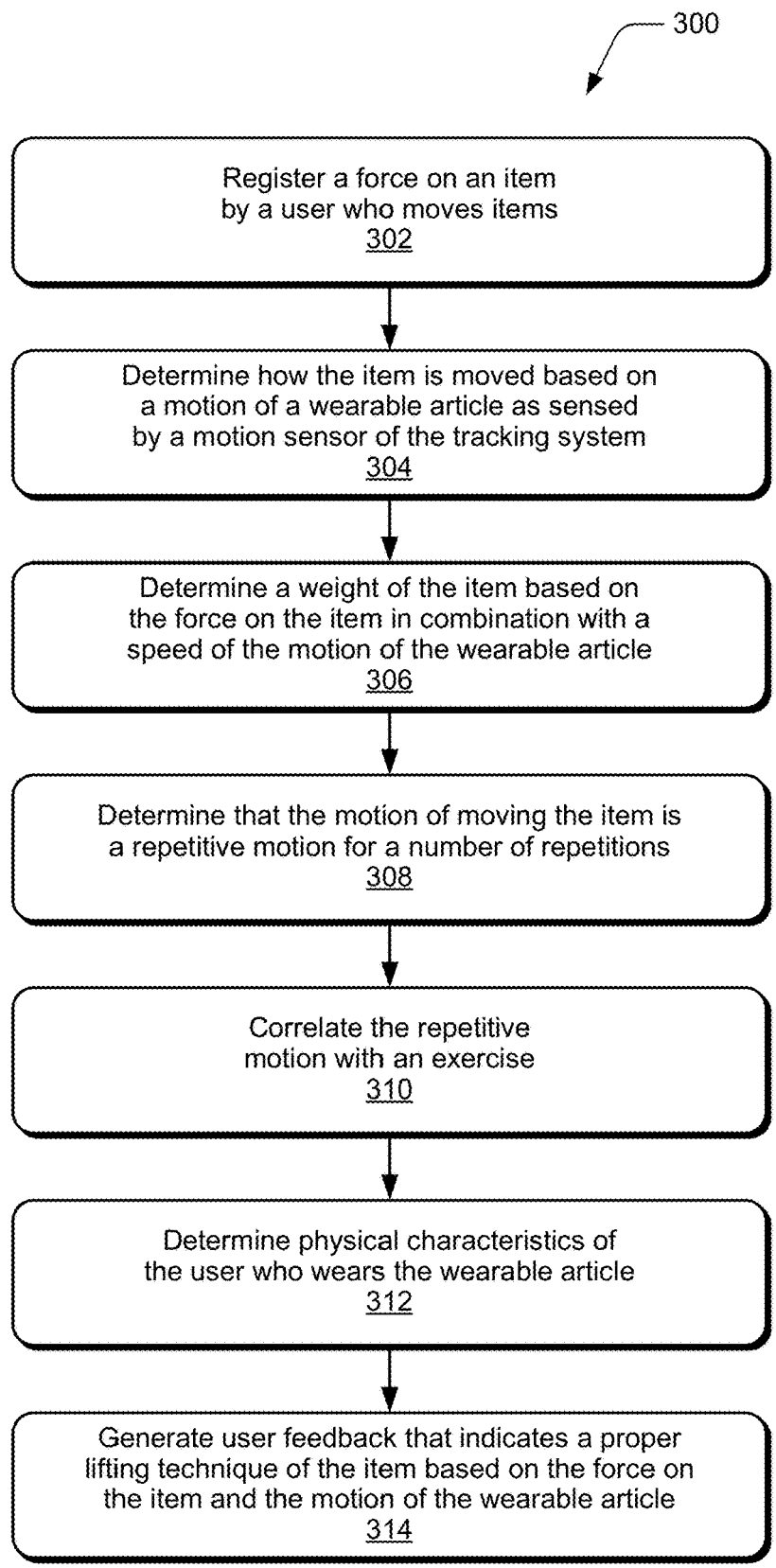
FIG. 3 illustrates example method(s) of a wireless hand sensory apparatus for weight monitoring in accordance with techniques described herein.

FIG. 3 illustrates example method(s) 300 of a wireless hand sensory apparatus for weight monitoring as described herein, and the method is generally described with reference to the tracking system implemented in a wearable article. The order in which the method is described is not intended to be construed as a limitation, and any number or combination of the described method operations can be performed in any order to perform a method, or an alternate method.

At 302, a force is registered, where the force on an item is by a user who moves items. For example, the tracking system 112 includes the force sensors 114 implemented in one or both of the gloves of the pair of gloves 102 (e.g., wearable articles) that are wearable by a user, and the force sensors register the force of a grasp on an item (e.g., a package 202) by the user who grasps, handles, and moves the item. The tracking system 112 can include multiple force sensors 114 that register the force of the grasp on the item, and the force sensors 114 in a glove (e.g., the right-hand glove 104 and/or the left-hand glove 106) can include a palm force sensor 116, or sensors, as well as finger force sensors 118.

At 304, a determination is made as to how the item is moved based on a motion of the wearable article as sensed by a motion sensor of the tracking system. For example, the tracking system 112 includes a motion sensor 128, or motion sensors, to sense motion of the glove as the user picks up and moves an item while wearing the pair of gloves 102. The tracking logic 138 that is implemented by the tracking system 112 determines how the item is moved based on a motion of the glove, or gloves 102, as sensed by the motion sensor 128 of the tracking system.

At 306, a weight of the item is determined based on the force on the item in combination with a speed of the motion of the wearable article. For example, the tracking logic 138 that is implemented by the tracking system 112 receives the force sensor inputs 140 from the force sensor 114, and optionally, receives the motion sensor inputs 142 from the motion sensor 128. The tracking logic 138 then determines the weight of an item based on the force of the grasp on the item in combination with a speed of the motion of the glove, or gloves 102.

At 308, the motion of moving the item is determined as a repetitive motion for a number of repetitions and, at 310, the repetitive motion is correlated with an exercise. For example, the tracking logic 138 that is implemented by the tracking system 112 determines that the motion of the item (e.g., as grasped by a user who is wearing the gloves 102) is a repetitive motion for a number of repetitions, such as by the user who lifts weights in a gym for exercise. The tracking logic 138 then correlates the repetitive motion with an exercise, such as based on a database that correlates particular motions with respective exercises.

At 312, physical characteristics of the user who wears the wearable article is determined. For example, the tracking logic 138 that is implemented by the tracking system 112 determines physical characteristics 210 of the user who wears the pair of gloves 102. The user physical characteristics 210 related to the user moving a package 202 can include an indication of the lifting technique 234 of the user who picks up and moves an item (e.g., a package, a weight, or any other type of item), the distance traveled 226 over a time duration by a user handling items or packages, and any other package handling activity 212, such as an indication of the user having an injury relating to lifting and moving items, efficiencies of lifting and movement (e.g., related to the lifting technique 234), as well as safety concerns and various other physical characteristics related to a user moving the package 202, or packages.

At 314, user feedback is generated that indicates a proper lifting technique of the item based on the force on the item and the motion of the wearable article. For example, the tracking logic 138 that is implemented by the tracking system 112 generates the user feedback 238 as any type of audio or visual feedback, such as for display on the integrated display device 218 of the device 208 to indicate a proper lifting technique of an item (e.g., weights in a gym, or packages handled for delivery) based on the force on the package 202 and the motion of the glove or gloves 102 as the user picks up and moves the package.

Figure 4:
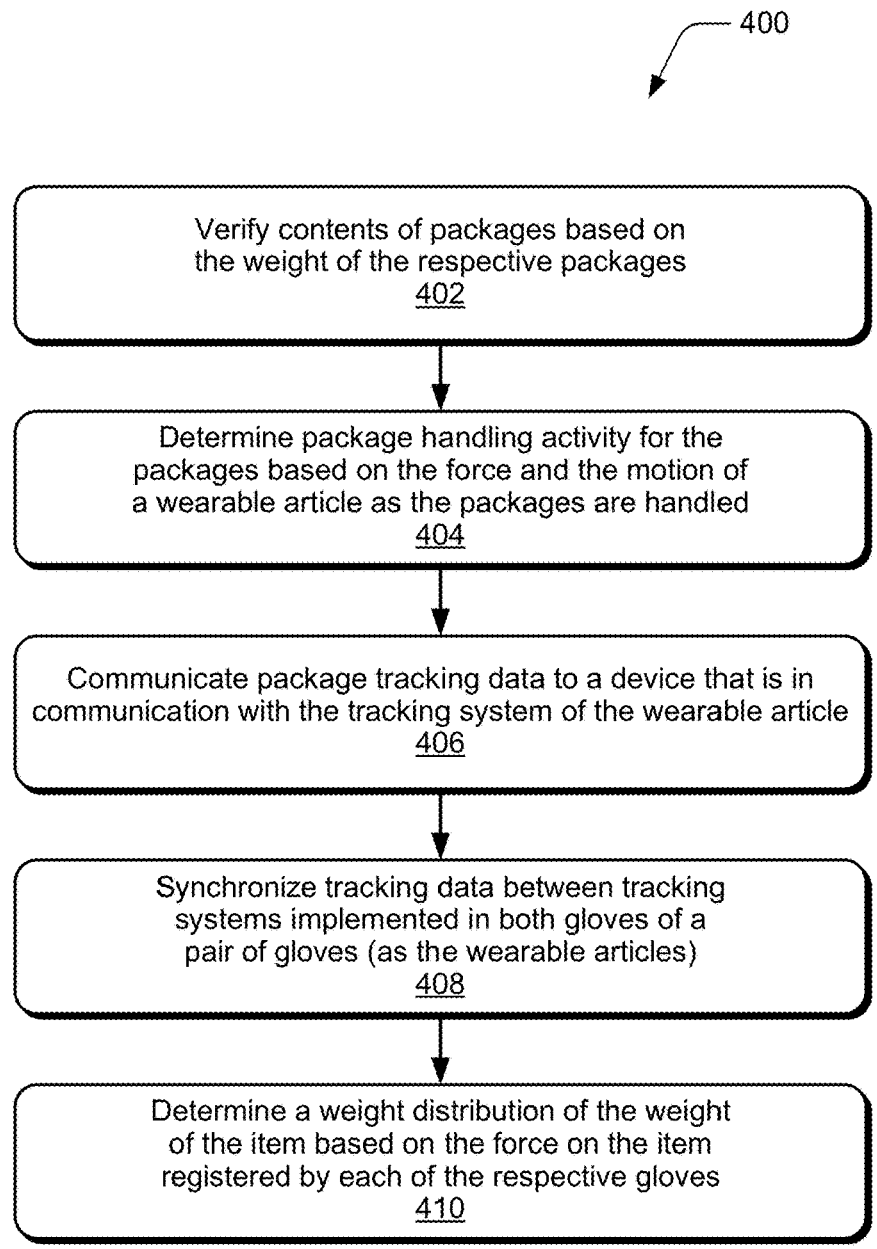
FIG. 4 illustrates example method(s) of a wireless hand sensory apparatus for weight monitoring in accordance with one or more embodiments.

FIG. 4 illustrates example method(s) 400 of a wireless hand sensory apparatus for weight monitoring as described herein, and the method is generally described with reference to the tracking system implemented in a wearable article. The order in which the method is described is not intended to be construed as a limitation, and any number or combination of the described method operations can be performed in any order to perform a method, or an alternate method.

At 402, contents of packages are verified based on the weight of the respective packages. For example, the items that are moved by a user may be packages, and the tracking logic 138 that is implemented by the tracking system 112 in the pair of gloves 102 (e.g., wearable articles) verifies or confirms the package contents based on a known weight of an item 222 or items in the package 202. The tracking logic 138 can also determine evidence of product tampering based on a different weight than the known weight of the item 222 or items in the package 202, and/or determine or verify other characteristics about a package.

At 404, package handling activity for the packages is determined based on the force and the motion of the wearable article as the packages are handled. For example, the tracking logic 138 that is implemented by the tracking system 112 in the pair of gloves 102 determines the package handling activity 212 based on the force and the motion of the glove, or gloves, as the packages 202 are handled. Information related to the package handling activity 212 can include a determination of repetitive motions, an indication of the user having an injury relating to lifting and moving items, efficiencies of lifting and movement (e.g., related to the lifting technique 234), as well as safety concerns and various other physical characteristics related to a user moving the packages 202.

At 406, package tracking data is communicated to a device that is in communication with the tracking system of the wearable article. For example, the tracking system 112 that is integrated in the right-hand glove 104, the left-hand glove 106, or in both gloves of the pair of gloves 102 includes the wireless radio system 134, which communicates (at 204) the tracking data 206 to another device 208 that is in communication with the tracking system 112 of the glove or gloves.

At 408, tracking data is synchronized between tracking systems implemented in both gloves of a pair of gloves (as wearable articles). For example, the tracking system 112 may be implemented in both gloves of the pair of gloves 102, and the wireless radio system 134 in each of the respective tracking systems 112 for the right-hand glove 104 and the left-hand glove 106 synchronize tracking data and the timing of data reporting between the tracking systems of the pair of gloves (at 144).

At 410, a weight distribution of the weight of the item is determined based on the force on the item registered by each of the respective gloves. For example, the tracking logic 138 determines a weight distribution of the weight of the item based on the force on the item registered by each of the tracking systems 112 integrated in the respective left-hand and right-hand gloves of the pair of gloves 102.

Figure 5:
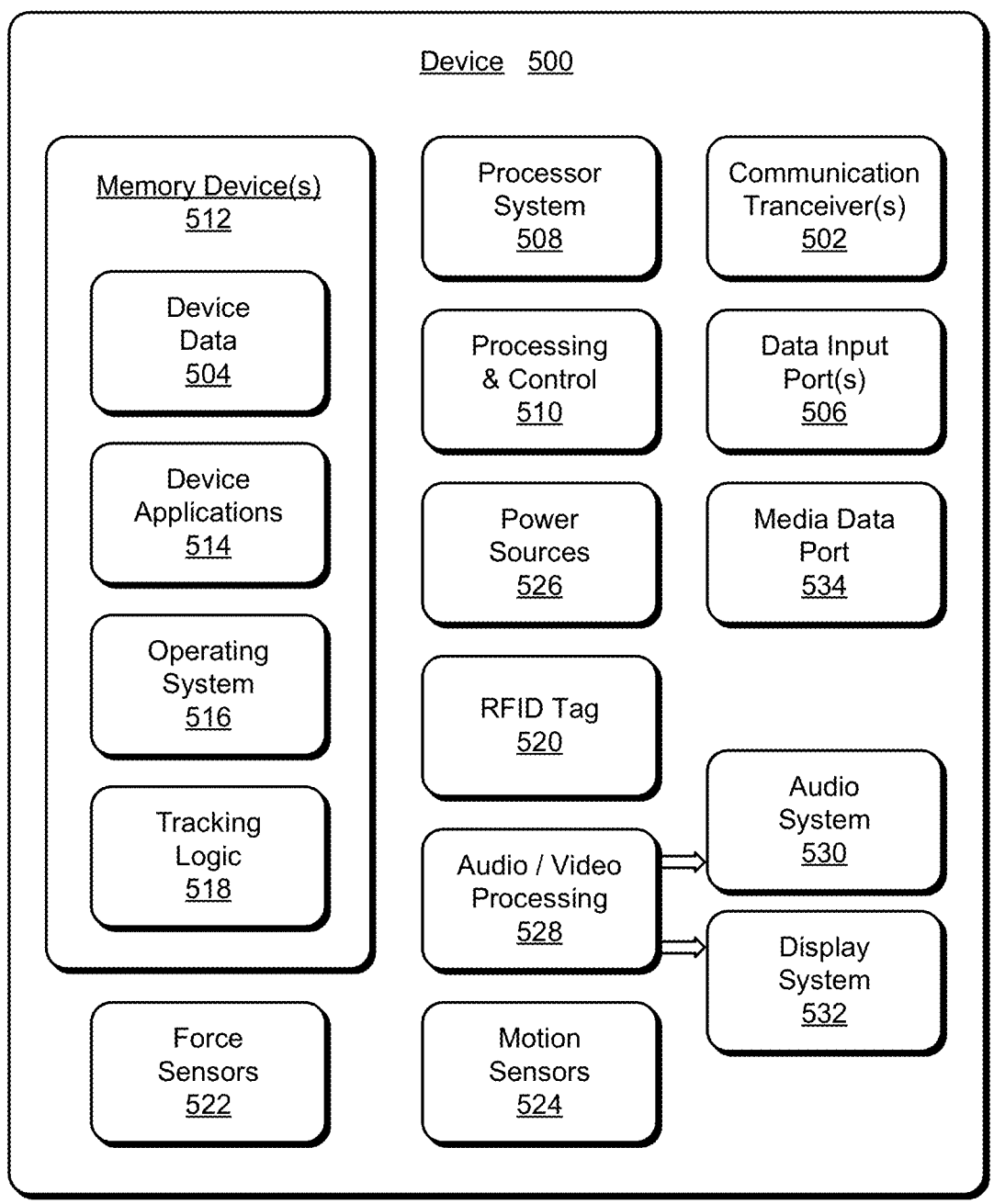
FIG. 5 illustrates various components of an example device that can implement aspects of a wireless hand sensory apparatus for weight monitoring.

FIG. 5 illustrates various components of an example device 500 in which aspects of a wireless hand sensory apparatus for weight monitoring can be implemented. The example device 500 can be implemented as any of the devices described with reference to the previous FIGS. 1-4, such as any type of client device, mobile phone, tablet, computing, communication, entertainment, gaming, media playback, and/or other type of electronic device, to include the tracking system 112 implemented as a "device" that is integrated in a wearable article, such as one or both of the gloves of the pair of gloves 102. For example, the tracking system 112 and the device 208 shown in FIGS. 1 and 2, as well as server devices, may be implemented as the example device 500.

The device 500 includes communication transceivers 502 that enable wired and/or wireless communication of device data 504 with other devices, such as tracking data, package tracking data, and information related to package handling activity as described with reference to FIGS. 1-4. Additionally, the device data can include any type of audio, video, and/or image data. Example transceivers include wireless personal area network (WPAN) radios compliant with various IEEE 802.15 (Bluetooth™) standards, wireless local area network (WLAN) radios compliant with any of the various IEEE 802.11 (WiFi™) standards, wireless wide area network (WWAN) radios for cellular phone communication, wireless metropolitan area network (WMAN) radios compliant with various IEEE 802.15 (WiMAX™ standards, and wired local area network (LAN) Ethernet transceivers for network data communication.

The device 500 may also include one or more data input ports 506 via which any type of data, media content, and/or inputs can be received, such as user-selectable inputs to the device, messages, music, television content, recorded content, and any other type of audio, video, and/or image data received from any content and/or data source. The data input ports may include USB ports, coaxial cable ports, and other serial or parallel connectors (including internal connectors) for flash memory, DVDs, CDs, and the like. These data input ports may be used to couple the device to any type of components, peripherals, or accessories such as microphones and/or cameras.

The device 500 includes a processing system 508 of one or more processors (e.g., any of microprocessors, controllers, and the like) and/or a processor and memory system implemented as a system-on-chip (SoC) that processes computer-executable instructions. The processor system may be implemented at least partially in hardware, which can include components of an integrated circuit or on-chip system, an application-specific integrated circuit (ASIC), a field-programmable gate array (FPGA), a complex programmable logic device (CPLD), and other implementations in silicon and/or other hardware. Alternatively or in addition, the device can be implemented with any one or combination of software, hardware, firmware, or fixed logic circuitry that is implemented in connection with processing and control circuits, which are generally identified at 510. The device 500 may further include any type of a system bus or other data and command transfer system that couples the various components within the device. A system bus can include any one or combination of different bus structures and architectures, as well as control and data lines.

The device 500 also includes computer-readable storage memory 512 (e.g., memory devices) that enable data storage, such as data storage devices that can be accessed by a computing device, and that provide persistent storage of data and executable instructions (e.g., software applications, programs, functions, and the like). Examples of the computer-readable storage memory 512 include volatile memory and non-volatile memory, fixed and removable media devices, and any suitable memory device or electronic data storage that maintains data for computing device access. The computer-readable storage memory can include various implementations of random access memory (RAM), read-only memory (ROM), flash memory, and other types of storage media in various memory device configurations. The device 500 may also include a mass storage media device.

The computer-readable storage memory 512 provides data storage mechanisms to store the device data 504, other types of information and/or data, and various device applications 514 (e.g., software applications). For example, an operating system 516 can be maintained as software instructions with a memory device and executed by the processing system 508. The device applications may also include a device manager, such as any form of a control application, software application, signal-processing and control module, code that is native to a particular device, a hardware abstraction layer for a particular device, and so on. In this example, the device 500 includes tracking logic 518 that implements aspects of a wireless hand sensory apparatus for weight monitoring, and may be implemented with hardware components and/or in software, such as when the device 500 is implemented as the tracking system 112 described with reference to FIGS. 1-4. An example of the tracking logic 518 is the tracking logic 138 that is implemented as an application or component in the tracking system 112.

The device 500 can also include a radio-frequency identification (RFID) tag 520, as well as force sensors 522 and motion sensors 524. The device 500 can also include one or more power sources 526, such as when the device is implemented as a mobile device (e.g., the tracking system 112 that is integrated into one or both of the gloves of the pair of gloves 102). The power sources may include a charging and/or power system, and can be implemented as a flexible strip battery, a rechargeable battery, a charged super-capacitor, and/or any other type of active or passive power source.

The device 500 also includes an audio and/or video processing system 528 that generates audio data for an audio system 530 and/or generates display data for a display system 532. The audio system and/or the display system may include any devices that process, display, and/or otherwise render audio, video, display, and/or image data. Display data and audio signals can be communicated to an audio component and/or to a display component via an RF (radio frequency) link, S-video link, HDMI (high-definition multimedia interface), composite video link, component video link, DVI (digital video interface), analog audio connection, or other similar communication link, such as media data port 534. In implementations, the audio system and/or the display system are integrated components of the example device. Alternatively, the audio system and/or the display system are external, peripheral components to the example device.

Although aspects of a wireless hand sensory apparatus for weight monitoring have been described in language specific to features and/or methods, the subject of the appended claims is not necessarily limited to the specific features or methods described. Rather, the specific features and methods are disclosed as example implementations of a wireless hand sensory apparatus for weight monitoring, and other equivalent features and methods are intended to be within the scope of the appended claims. Further, various different embodiments are described and it is to be appreciated that each described embodiment can be implemented independently or in connection with one or more other described embodiments. Additional aspects of the techniques, features, and/or methods discussed herein relate to one or more of the following embodiments.

A system comprising: a wearable article worn by a user who moves items; a tracking system implemented in the wearable article, the tracking system comprising: at least one force sensor to register a force on an item; and tracking logic that determines a weight of the item based on the force on the item.

Alternatively or in addition to the above described system, any one or combination of: The item is a package for delivery; and the tracking logic verifies contents of the package based on the weight of the package. The system further comprises a motion sensor to sense motion of the wearable article; and wherein the tracking logic determines how the item is moved based on the motion of the wearable article. The tracking logic determines the weight of the item based on the force on the item in combination with a speed of the motion of the wearable article. The tracking logic generates user feedback that indicates a proper lifting technique of the item based on the force on the item and the motion of the wearable article. The tracking logic determines that the motion is a repetitive motion for a number of repetitions, and correlates the repetitive motion with an exercise. The item is a package for delivery; and the tracking logic determines package handling activity for the package based on the force and the motion of the wearable article as the package is handled. The tracking logic determines one or more physical characteristics of the user who wears the wearable article. The one or more physical characteristics of the user include a lifting technique of the user to lift and move the item. The system further comprises a motion sensor to sense motion of the wearable article; and wherein the one or more physical characteristics of the user include a distance traveled over a time duration. The tracking system comprises a wireless radio system to communicate tracking data to a device that is in communication with the tracking system of the wearable article. The wearable article is a glove of a pair of gloves, and the tracking system comprises multiple force sensors that register the force on the item, the multiple force sensors in the glove including at least one palm force sensor and finger force sensors. The wearable article is a pair of gloves; the tracking system is implemented in both gloves of the pair of gloves; and the tracking system comprises a wireless radio system to synchronize tracking data between the tracking systems of the pair of gloves. The tracking logic determines a weight distribution of the weight of the item based on the force on the item registered by each of the respective gloves.

A method comprising: registering a force on an item by a user who moves items, said registering the force with a force sensor of a tracking system implemented in a wearable article worn by the user; determining how the item is moved based on a motion of the wearable article as sensed by a motion sensor of the tracking system; and determining a weight of the item based on the force on the item in combination with a speed of the motion of the wearable article.

Alternatively or in addition to the above described method, any one or combination of: The items are packages for delivery, and the method further comprising verifying contents of the packages based on the weight of the respective packages. The method further comprising generating user feedback that indicates a proper lifting technique of the item based on the force on the item and the motion of the wearable article. The method further comprising determining one or more physical characteristics of the user who wears the wearable article, including at least a lifting technique of the user to lift and move the item.

A pair of gloves comprising: force sensors to register a force on an item by a user who moves items wearing the pair of gloves; a motion sensor to sense motion of the pair of gloves; and a processing system to execute tracking logic that determines a weight of the item based on the force on the item and based on a speed of the motion of the pair of gloves.

Alternatively or in addition to the above described pair of gloves, any one or combination of: The items are packages for delivery; and the tracking logic determines package handling activity for the packages based on the force and the motion of the pair of gloves as the packages are handled.

The invention claimed is:
1. A system, comprising:
a wearable article worn by a user who moves items;
a tracking system implemented with a processing system and integrated in the wearable article, the tracking system comprising:
at least one force sensor to register a force applied to an item by the user wearing the wearable article and holding the item;
tracking logic implemented by the processing system at least partially in computer hardware to:
determine a weight of the item based on the applied force by the user on the item;
verify that the item is intended for handling by the user based on a comparison of a known weight of the item to the determined weight; and
generate a displayable verification that the item is the intended item.

2. The system as recited in claim 1, wherein:
the item is a package for delivery; and
the tracking logic verifies contents of the package based on the determined weight of the package.

3. The system as recited in claim 1, further comprising:
a motion sensor integrated in the wearable article to sense motion of the wearable article; and
wherein the tracking logic determines how the item is moved based on the motion of the wearable article.

4. The system as recited in claim 3, wherein the tracking logic determines the weight of the item based on the applied force by the user on the item in combination with a speed of the motion of the wearable article.

5. The system as recited in claim 3, wherein the tracking logic generates user feedback that indicates a proper lifting technique of the item based on the applied force by the user on the item and the motion of the wearable article.

6. The system as recited in claim 3, wherein the tracking logic determines that the motion is a repetitive motion for a number of repetitions, and correlates the repetitive motion with an exercise based on a database that correlates particular motions with respective exercises.

7. The system as recited in claim 3, wherein:
the item is a package for delivery; and
the tracking logic determines package handling activity for the package based on the applied force and the motion of the wearable article as the package is handled.

8. The system as recited in claim 1, wherein the tracking logic determines one or more physical characteristics of the user who wears the wearable article.

9. The system as recited in claim 8, wherein the one or more physical characteristics of the user include a lifting technique of the user to lift and move the item.

10. The system as recited in claim 8, further comprising:
a motion sensor integrated in the wearable article to sense motion of the wearable article; and
wherein the one or more physical characteristics of the user include a distance traveled over a time duration.

11. The system as recited in claim 1, wherein the tracking system comprises a wireless radio system to communicate tracking data to a device that is in communication with the tracking system of the wearable article.

12. The system as recited in claim 1, wherein the wearable article is a glove of a pair of gloves, and the tracking system comprises multiple force sensors integrated in the glove to register the applied force by the user on the item, the multiple force sensors in the glove including at least one palm force sensor and finger force sensors.

13. The system as recited in claim 1, wherein:
the wearable article is a pair of gloves;

the tracking system is implemented in both gloves of the pair of gloves; and the tracking system comprises a wireless radio system to synchronize tracking data between the tracking systems of the pair of gloves.

14. The system as recited in claim 13, wherein the tracking logic determines a weight distribution of the determined weight of the item based on the applied force by the user on the item registered by each of the respective gloves.

15. The system of claim 1, wherein the tracking logic is configured to determine that the item has been tampered with based on the determined weight of the item having a different weight than the known weight of the item.

16. A method, comprising:
registering a force applied to an item by a user who moves items, the force being registered with a force sensor of a tracking system implemented in a wearable article worn by the user;
determining how the item is moved based on a motion of the wearable article as sensed by a motion sensor of the tracking system, the motion sensor integrated in the wearable article;
determining, using tracking logic implemented with a processor of the tracking system that is implemented in the wearable article, a weight of the item based on the applied force by the user on the item in combination with a speed of the motion of the wearable article; and
verifying that the item is intended for handling by the user by comparing a known weight of the item to the determined weight.

17. The method as recited in claim 16, further comprising:
generating user feedback that indicates a proper lifting technique of the item based on the applied force by the user on the item and the motion of the wearable article.

18. The method as recited in claim 16, further comprising:
determining one or more physical characteristics of the user who wears the wearable article, including at least a lifting technique of the user to lift and move the item.

19. A pair of gloves, comprising:
force sensors integrated in the pair of gloves to register a force applied to an item by a user who moves items wearing the pair of gloves;
a motion sensor integrated in one of the gloves to sense motion of the one glove of the pair of gloves; and
a processing system to execute tracking logic at least partially in computer hardware, the tracking logic implemented to:
determine a weight of the item based on the applied force by the user on the item and based on a speed of the motion of the pair of gloves; and
verify that the item is intended for handling by the user by comparing a known weight of the item to the determined weight.

20. The pair of gloves as recited in claim 19, wherein:
the items are packages for delivery; and
the tracking logic determines package handling activity for the packages based on the applied force by the user and the motion of the pair of gloves as the packages are handled.

* * * * *